US00PP09911P

United States Patent [19]

Bergman

[11] Patent Number: Plant 9,911

[45] Date of Patent: Jun. 3, 1997

[54] AZALEA PLANT NAMED SACHET

[75] Inventor: Wendy R. Bergman, Lehigh Acres, Fla.

[73] Assignee: Yoder Brothers, Inc., Barberton, Ohio

[21] Appl. No.: 583,477

[22] Filed: Jan. 5, 1996

[51] Int. Cl.[6] ..... A01H 5/00

[52] U.S. Cl. ..... Plt./57

[58] Field of Search ..... Plt./55, 56, 57

*Primary Examiner*—James R. Feyrer

*Attorney, Agent, or Firm*—Foley & Lardner

[57] ABSTRACT

An azalea plant named Sachet particularly characterized by its evergreen foliage, hose-in-hose flower form with frilled margins, dark bright pink flower color, ease of budding, uniform and dense plant habit, free branching, rapid and uniform flower response in a year round controlled program, excellent cooler tolerance and keeping quality.

1 Drawing Sheet

The present invention comprises a new and distinct cultivar of Azalea, a greenhouse forcing type, hereinafter referred to as Sachet.

Sachet, identified as Code 1002 during the selection process, originated from a planned cross hybridization between two selected breeding lines in a controlled breeding program in Fort Myers, Fla.

The female, or seed parent of Sachet is the commercial cultivar Girard's Fushia, a deep reddish purple single. The male, or pollen parent is a seedling known as Code 227, a proprietary breeding line.

Sachet was discovered and selected by Wendy R. Bergman as one flowering plant within the progeny of the stated cross in January 1992, in Fort Myers, Fla.

The first asexual reproduction of Sachet was accomplished when vegetative cuttings were taken from the initial selection in April 1992, in Fort Myers, Fla., by technicians working under formulations established and supervised by Wendy R. Bergman.

Horticultural examination of controlled flowerings of successive generations of plants derived from cuttings taken from the original selection has shown that the unique combination of characteristics as herein disclosed for Sachet are fixed and retained through successive generations of asexual reproduction.

Sachet has not been observed under all possible environmental conditions. The phenotype may vary significantly with variations in environment such as temperature, light intensity and day length, without, however, any variance in the genotype.

The following observations, measurements and comparisons describe plants that were grown in Fort Myers, Fla. in a controlled greenhouse environment and following a commercial schedule.

The following traits have been repeatedly observed and are determined to be basic characteristics of Sachet, which, in combination, distinguish this azalea as a new and distinct cultivar:

1. A bright, dark pink flower color (66B) fading to medium pink (64D) at old age.
2. Hose-in-hose flower form with a ruffled petal margin.
3. The flowers range in size from 6.0 to 8.0 cm in diameter with 7.0 cm the average size.
4. Compact, uniform and symmetrical plant habit.
5. Fast, uniform response in a year round controlled flowering program, forcing in 28 days on average.
6. Excellent longevity in a simulated home environment, with flowers lasting up to 36 days.
7. Excellent foliage retention and no flower bud damage when cooled for 6 weeks with no lighting at 38° F.

The accompanying color photograph shows in perspective view the unique features of the new cultivar, wih colors being as true as possible with color illustrations of this type.

Of the commerical cultivars known to the inventor, the most similar in comparison to Sachet is Solitaire disclosed in U.S. Plant Pat. No. 3,171. Sachet is similar to Solitaire in that both are pink evergreen azaleas suitable for greenhouse forcing.

Sachet differs from Solitaire in that Sachet's flowers are darker pink, have a distinct blotch, and do not possess petaloid anthers like those of Solitaire. the plant habit of Sachet is much denser and more heavily branched than that of Solitaire.

In the following description color references are made to The Royal Horticultural Society Colour Chart. The color values were determined on Mar. 13, 1995. All readings were taken in an office under cool white fluorescent lights, facing a west window between the hours of 10:00 a.m and 2:00 p.m.

Classification:

*Botanical.*—Rhododendron hybrida, evergreen type.

*Commercial.*—Florist forcing pot azalea, cv. Sachet.

Inflorescence

Flower (General):

*Size.*—6.0 to 8.0 cm.

*Born.*—Terminal cluster, usually three (3) per bud, ranging from two to four (2–4). Occasionally more than one bud per stem.

*Form.*—Hose-in-hose. Funnel-form.

*Blooming habit.*—Once profusely. Buds easily and uniformly in a year-round flowering program. The majority of terminal buds break color within one (1) week of the first. Flowering begins approximately 28 days after the start of forcing.

*Fragrance.*—Present.

Corolla (petals):

*Texture.*—Soft.

*Substance.*—Heavy.

*Shape.*—Rounded with slightly frilled margin.

*Color (fully open).*—Generally 66B, bright dark pink. Upper surface: Edge: 66B. Center: 66B. Base: 39D. Lower surface: 66C. Blotch: 63A.

Bud:

*Size.*—Medium.

*Shape.*—Conoidal.

*Color.*—67C.

*Bud sheath.*—Light green with light brown hairs.

Calyx:

*Form.*—Enlarged and transformed into petals, (hose-in-hose) irregular shape.

*Color.*—66B.

Peduncle:

*Length.*—0.5–1.5 cm.

*Strength.*—Strong.

*Aspect.*—Pubescent.

Reproductive organs:

*Androecium* (*stamens*).—Number: Five (5). Anthers: 183B. Filaments: Length: 2–3.5 cm. Color: 64C.

*Gynoecium* (*pistil*).—Stigma: Between 60A and 60B. Style: Length: 2.0–3.5 cm. Color: 61C. Ovary: Pubescent.

Plant Characteristics

Foliage:

*Type.*—Evergreen.

*Arangement.*—Alternate.

*Shape.*—Elliptic.

Size.—Length: 2.0–6.5 cm. Width: 1.0–2.6 cm.

*Margin.*—Entire.

*Color.*—Immature: Upper surface: 144A. Lower surface: 144A, slightly whiter. Mature: Upper surface: 139A. Lower surface: 146B. Texture: Leathery. Tomentum: Present on upper surface. Insignificant.

Stems:

*Color.*—Immature: 146D. Mature: 165B. Tomentum: Present, dark golden-brown. Insignificant.

Plant habit: Compact, semi-upright, dense bush which is uniform and symmetrical in a six-inch (6") pot when pinched three (3) times. Total crop time to the dormant budded stage is 40–42 weeks to produce a plant approximately 30 cm in diameter and having a total height of 30–36 cm. Internode lengths vary widely from 2–20 mm on the same stem.

Branching habit: Free branching, producing three to five (3–5) breaks when a vegetative cutting is pinched.

Rooting: Roots easily in eight to ten (8–10) weeks with 75° F. soil temperature.

Budding ease: Plants produce flower buds easily and uniformly year round with the use of commercially available plant growth regulators. Natural season response has not been acertained.

Cooler tolerance: Plants placed in a cooler as a means of breaking dormancy perform very well. Sachet is tolerant of six (6) weeks in an unlighted cooler at 38° F. without excessive bud damage or foliage loss.

Blooming: Plants reach the stage of 12 buds showing color in 28 days on average after the cooling treatment. This varies from 19 to 36 days depending upon time of year. Sachet flowers uniformly and profusely across the plant.

Shelf life: When plants are moved to an office or home environment at the state of eight (8) open flowers, they maintain an attractive appearance for 36 days on average.

It is claimed:

1. A new and distinct cultivar of azalea named Sachet, as described and illustrated.

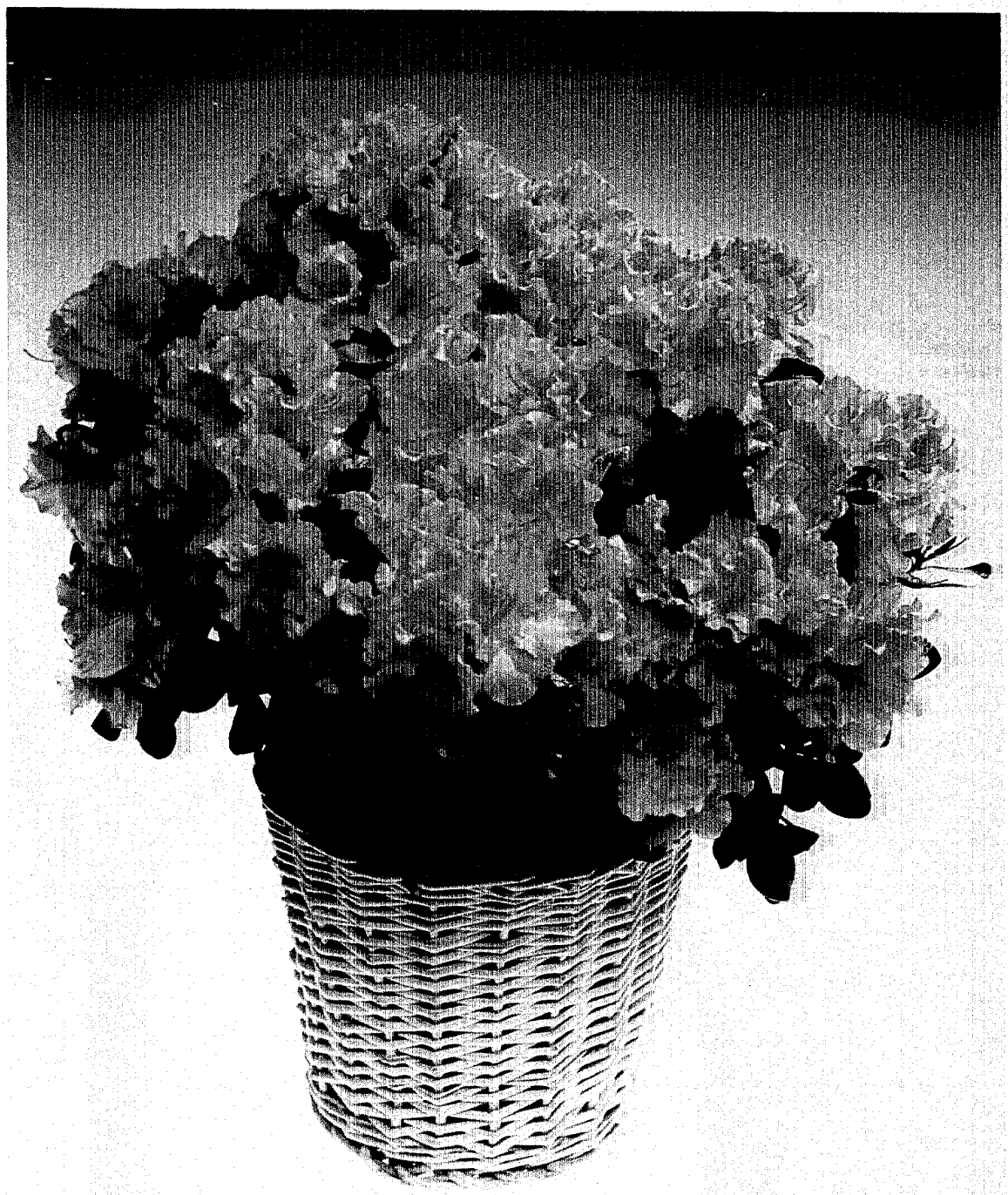

* * * * *